United States Patent
Arcot-Krishnamurthy et al.

(10) Patent No.: US 8,548,586 B2
(45) Date of Patent: *Oct. 1, 2013

(54) CONFIGURABLE INTERMITTENT PACING THERAPY

(75) Inventors: Shantha Arcot-Krishnamurthy, Roseville, MN (US); John R. Zielinski, Eagan, MN (US); Joseph M. Pastore, Mentor, OH (US); Jeffrey E. Stahmann, Ramsey, MN (US); Allan C. Shuros, St. Paul, MN (US); Robert Shipley, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 822 days.

This patent is subject to a terminal disclaimer.

(21) Appl. No.: 12/361,353

(22) Filed: Jan. 28, 2009

(65) Prior Publication Data

US 2009/0192560 A1 Jul. 30, 2009

Related U.S. Application Data

(60) Provisional application No. 61/024,431, filed on Jan. 29, 2008.

(51) Int. Cl.
*A61N 1/362* (2006.01)
(52) U.S. Cl.
USPC .................................. 607/9; 607/17
(58) Field of Classification Search
USPC .............. 600/508–509, 512, 513, 515–517; 607/2–3, 9, 14–19, 25–28
See application file for complete search history.

(56) References Cited

U.S. PATENT DOCUMENTS

| 4,587,975 A | 5/1986 | Salo et al. |
| 4,730,619 A | 3/1988 | Koning et al. |

(Continued)

FOREIGN PATENT DOCUMENTS

| AU | 2009209397 | 11/2012 |
| EP | 1437159 A1 | 7/2004 |

(Continued)

OTHER PUBLICATIONS

"U.S. Appl. No. 11/030,575, Non Final Office Action mailed Jul. 26, 2006", 10 pgs.

(Continued)

*Primary Examiner* — Rex R Holmes
(74) *Attorney, Agent, or Firm* — Schwegman Lundberg & Woessner, P.A.

(57) ABSTRACT

This document discusses, among other things, an apparatus comprising at least one implantable cardiac depolarization sensing circuit, an electrical stimulation circuit, and a pacing mode controller. The implantable cardiac depolarization sensing circuit is configured to obtain a sensed depolarization signal from a ventricle and the electrical stimulation circuit is configured to provide pacing electrical stimulation energy to at least one implantable ventricular electrode. The pacing mode controller delivers pacing therapy according to a first pacing mode that is a normal operating mode, and delivers pacing therapy according to second and third pacing modes. The second and third pacing modes increase mechanical stress on at least a particular portion of the ventricle as compared to the pacing therapy delivered during the first pacing mode. The pacing mode controller alternates between the second and third pacing modes when switched from the normal operating mode to a stress augmentation mode.

35 Claims, 6 Drawing Sheets

(56) References Cited

U.S. PATENT DOCUMENTS

| | | |
|---|---|---|
| 4,773,401 A | 9/1988 | Citak et al. |
| 4,834,710 A | 5/1989 | Fleck |
| 4,872,459 A | 10/1989 | Pless et al. |
| 4,919,133 A | 4/1990 | Chiang |
| 5,007,427 A | 4/1991 | Suzuki et al. |
| 5,072,458 A | 12/1991 | Suzuki |
| 5,111,818 A | 5/1992 | Suzuki et al. |
| 5,135,004 A | 8/1992 | Adams et al. |
| 5,178,149 A | 1/1993 | Imburgia et al. |
| 5,184,615 A | 2/1993 | Nappholz et al. |
| 5,199,428 A | 4/1993 | Obel et al. |
| 5,203,326 A | 4/1993 | Collins |
| 5,282,840 A | 2/1994 | Hudrlik |
| 5,313,953 A | 5/1994 | Yomtov et al. |
| 5,376,106 A | 12/1994 | Stahmann et al. |
| 5,447,529 A | 9/1995 | Marchlinski et al. |
| 5,484,419 A | 1/1996 | Fleck |
| 5,531,768 A | 7/1996 | Alferness |
| 5,588,432 A | 12/1996 | Crowley |
| 5,634,899 A | 6/1997 | Shapland et al. |
| 5,755,671 A | 5/1998 | Albrecht et al. |
| 5,919,209 A | 7/1999 | Schouten |
| 6,021,350 A | 2/2000 | Mathson |
| 6,076,015 A | 6/2000 | Hartley et al. |
| 6,108,577 A | 8/2000 | Benser |
| 6,115,628 A | 9/2000 | Stadler et al. |
| 6,231,516 B1 | 5/2001 | Keilman et al. |
| 6,233,486 B1 | 5/2001 | Ekwall et al. |
| 6,238,422 B1 | 5/2001 | Oort |
| 6,256,538 B1 | 7/2001 | Ekwall |
| 6,272,379 B1 | 8/2001 | Fischell et al. |
| 6,285,907 B1 | 9/2001 | Kramer et al. |
| 6,314,323 B1 | 11/2001 | Ekwall |
| 6,368,284 B1 | 4/2002 | Bardy |
| 6,408,208 B1 | 6/2002 | Sun |
| 6,411,845 B1 | 6/2002 | Mower |
| 6,445,953 B1 | 9/2002 | Bulkes et al. |
| 6,477,402 B1 | 11/2002 | Lynch et al. |
| 6,493,579 B1 | 12/2002 | Gilkerson et al. |
| 6,501,983 B1 | 12/2002 | Natarajan et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,763,267 B2 | 7/2004 | Ding |
| 6,827,690 B2 | 12/2004 | Bardy |
| 6,838,471 B2 | 1/2005 | Tracey |
| 6,842,642 B2 | 1/2005 | Vanhout |
| 6,845,267 B2 | 1/2005 | Harrison et al. |
| 6,865,420 B1 | 3/2005 | Kroll |
| 6,882,883 B2 | 4/2005 | Condie et al. |
| 6,889,081 B2 | 5/2005 | Hsu |
| 6,892,095 B2 | 5/2005 | Salo |
| 6,907,285 B2 | 6/2005 | Denker et al. |
| 6,913,577 B2 | 7/2005 | Bardy |
| 6,937,899 B2 | 8/2005 | Sheldon et al. |
| 6,950,701 B2 | 9/2005 | Begemann et al. |
| 6,957,104 B2 | 10/2005 | Wagner |
| 6,965,797 B2 | 11/2005 | Pastore et al. |
| 6,973,349 B2 | 12/2005 | Salo |
| 7,003,350 B2 | 2/2006 | Denker et al. |
| 7,010,345 B2 | 3/2006 | Hill et al. |
| 7,025,730 B2 | 4/2006 | Cho et al. |
| 7,039,462 B2 | 5/2006 | Pastore et al. |
| 7,062,314 B2 | 6/2006 | Zhu et al. |
| 7,062,325 B1 | 6/2006 | Krig et al. |
| 7,069,070 B2 | 6/2006 | Carlson et al. |
| 7,072,711 B2 | 7/2006 | Girouard et al. |
| 7,215,992 B2 | 5/2007 | Stahmann et al. |
| 7,215,997 B2 | 5/2007 | Yu et al. |
| 7,236,821 B2 | 6/2007 | Cates et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,333,854 B1 | 2/2008 | Brewer et al. |
| 7,340,303 B2 | 3/2008 | Zhu |
| 7,364,547 B2 | 4/2008 | Stahmann et al. |
| 7,366,568 B2 | 4/2008 | Pastore et al. |
| 7,437,191 B2 | 10/2008 | Pastore et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,668,594 B2 | 2/2010 | Brockway et al. |
| 7,962,208 B2 | 6/2011 | Shuros et al. |
| 8,027,723 B2 | 9/2011 | Pastore et al. |
| 8,140,155 B2 | 3/2012 | Zielinski et al. |
| 8,214,040 B2 | 7/2012 | Pastore et al. |
| 8,306,615 B2 | 11/2012 | Brockway et al. |
| 2002/0026222 A1 | 2/2002 | Schauerte et al. |
| 2002/0042632 A1 | 4/2002 | Iaizzo et al. |
| 2002/0072777 A1 | 6/2002 | Lu |
| 2002/0082660 A1 | 6/2002 | Stahmann et al. |
| 2002/0123772 A1 | 9/2002 | Sun et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0060854 A1 | 3/2003 | Zhu |
| 2003/0105493 A1 | 6/2003 | Salo |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0158583 A1 | 8/2003 | Burnett et al. |
| 2003/0158584 A1 | 8/2003 | Cates et al. |
| 2003/0195572 A1 | 10/2003 | Bocek et al. |
| 2003/0199956 A1 | 10/2003 | Struble et al. |
| 2003/0204206 A1 | 10/2003 | Padua et al. |
| 2003/0204231 A1 | 10/2003 | Hine et al. |
| 2003/0233130 A1 | 12/2003 | Padmanabhan et al. |
| 2003/0233132 A1 | 12/2003 | Pastore et al. |
| 2004/0015081 A1 | 1/2004 | Kramer et al. |
| 2004/0038947 A1 | 2/2004 | Wink et al. |
| 2004/0049235 A1 | 3/2004 | Deno et al. |
| 2004/0088015 A1 | 5/2004 | Casavant et al. |
| 2004/0088017 A1 | 5/2004 | Sharma et al. |
| 2004/0102815 A1 | 5/2004 | Balczewski et al. |
| 2004/0106960 A1 | 6/2004 | Siejko et al. |
| 2004/0106961 A1 | 6/2004 | Siejko et al. |
| 2004/0133247 A1 | 7/2004 | Stahmann et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0075673 A1 | 4/2005 | Warkentin et al. |
| 2005/0090719 A1 | 4/2005 | Scheiner et al. |
| 2005/0096705 A1 | 5/2005 | Pastore et al. |
| 2005/0096706 A1 | 5/2005 | Salo |
| 2005/0137631 A1 | 6/2005 | Yu et al. |
| 2005/0143779 A1 | 6/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0288721 A1 | 12/2005 | Girouard et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0195038 A1 | 8/2006 | Carlson et al. |
| 2006/0206158 A1 | 9/2006 | Wu et al. |
| 2006/0241704 A1 | 10/2006 | Shuros et al. |
| 2006/0247686 A1 | 11/2006 | Girouard et al. |
| 2006/0247700 A1 | 11/2006 | Jackson |
| 2006/0253156 A1* | 11/2006 | Pastore et al. .................... 607/9 |
| 2006/0259087 A1 | 11/2006 | Baynham et al. |
| 2006/0259088 A1 | 11/2006 | Pastore et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0038261 A1 | 2/2007 | Kieval et al. |
| 2007/0043393 A1 | 2/2007 | Brockway et al. |

| | | | |
|---|---|---|---|
| 2007/0054871 A1 | 3/2007 | Pastore et al. | |
| 2007/0060972 A1 | 3/2007 | Kieval et al. | |
| 2007/0142871 A1 | 6/2007 | Libbus et al. | |
| 2007/0150005 A1 | 6/2007 | Sih et al. | |
| 2007/0162081 A1 | 7/2007 | Yu et al. | |
| 2007/0179392 A1 | 8/2007 | Zhang | |
| 2007/0239218 A1 | 10/2007 | Carlson et al. | |
| 2007/0260284 A1 | 11/2007 | Pastore et al. | |
| 2007/0282380 A1 | 12/2007 | Brooke et al. | |
| 2007/0299356 A1 | 12/2007 | Wariar et al. | |
| 2008/0015659 A1 | 1/2008 | Zhang et al. | |
| 2008/0021507 A1 | 1/2008 | Libbus et al. | |
| 2008/0027495 A1 | 1/2008 | Prinzen et al. | |
| 2008/0058661 A1 | 3/2008 | Bardy | |
| 2008/0058881 A1 | 3/2008 | Wagner et al. | |
| 2008/0077187 A1 | 3/2008 | Levin et al. | |
| 2008/0081354 A1 | 4/2008 | Qu et al. | |
| 2008/0082135 A1 | 4/2008 | Arcot-Krishnamurthy et al. | |
| 2008/0091138 A1 | 4/2008 | Pastore et al. | |
| 2008/0132972 A1 | 6/2008 | Shuros et al. | |
| 2008/0140141 A1 | 6/2008 | Ben-David et al. | |
| 2008/0177156 A1 | 7/2008 | Zhang et al. | |
| 2008/0177191 A1 | 7/2008 | Patangay et al. | |
| 2008/0177194 A1 | 7/2008 | Zhang et al. | |
| 2008/0215105 A1 | 9/2008 | Pastore et al. | |
| 2008/0221636 A1 | 9/2008 | Pastore et al. | |
| 2008/0234772 A1 | 9/2008 | Shuros et al. | |
| 2008/0234774 A1 | 9/2008 | Baynham et al. | |
| 2009/0025459 A1 | 1/2009 | Zhang et al. | |
| 2009/0043348 A1 | 2/2009 | Pastore et al. | |
| 2009/0048641 A1 | 2/2009 | Libbus | |
| 2009/0082781 A1 | 3/2009 | Tran et al. | |
| 2009/0234401 A1 | 9/2009 | Zielinski et al. | |
| 2009/0234416 A1 | 9/2009 | Zielinski et al. | |
| 2010/0121391 A1 | 5/2010 | Brockway et al. | |
| 2011/0230928 A1 | 9/2011 | Shuros et al. | |

FOREIGN PATENT DOCUMENTS

| | | | |
|---|---|---|---|
| JP | 7504597 A | 5/1995 | |
| JP | 2002514478 A | 5/2002 | |
| JP | 2004533297 A | 11/2004 | |
| WO | WO-95/18649 A1 | 7/1995 | |
| WO | WO-9958191 A1 | 11/1999 | |
| WO | WO-0115609 A1 | 3/2001 | |
| WO | WO-01/28625 A1 | 4/2001 | |
| WO | WO-01/76689 A2 | 10/2001 | |
| WO | WO-2004/058326 A2 | 7/2004 | |
| WO | WO-2005030325 A1 | 4/2005 | |
| WO | WO-2005/042091 A1 | 5/2005 | |
| WO | WO-2005042083 A2 | 5/2005 | |
| WO | WO-2006/079010 A1 | 7/2006 | |
| WO | WO-2006074189 A1 | 7/2006 | |
| WO | WO-2006/115693 A2 | 11/2006 | |
| WO | WO-2006/121842 A2 | 11/2006 | |
| WO | WO-2006/124636 A2 | 11/2006 | |
| WO | WO-2006/124729 A2 | 11/2006 | |
| WO | WO-2006121842 A3 | 11/2006 | |
| WO | WO-2007/078410 A1 | 7/2007 | |
| WO | WO-2007/133962 A2 | 11/2007 | |
| WO | WO-2007130774 A2 | 11/2007 | |
| WO | WO-2009/097118 A1 | 8/2009 | |
| WO | WO-2009117086 A2 | 9/2009 | |

OTHER PUBLICATIONS

"U.S. Appl. No. 11/030,575, Response filed Oct. 26, 2006 to Non Final Office Action mailed Jul. 26, 2006", 8 pgs.

"U.S. Appl. No. 11/151,015, Non Final Office Action mailed May 21, 2007", 10 pgs.

"U.S. Appl. No. 11/151,015, Response filed Aug. 21, 2007 to Non-Final Office Action mailed May 21, 2007", 9 pgs.

"U.S. Appl. No. 11/318,263, Non-Final Office Action mailed Aug. 20, 2008", 10 pgs.

"U.S. Appl. No. 11/318,263, Response filed May 22, 2008 to Restriction Requirement mailed Apr. 23, 2008", 10 pgs.

"U.S. Appl. No. 11/318,263, Response filed Nov. 20, 2008 to Non-Final Office Action mailed Aug. 20, 2008", 12 pgs.

"International Application Serial No. PCT/US2006/017384, International Search Report and Written Opinion mailed Jan. 23, 2007", 12 pgs.

"International Application Serial No. PCT/US2007/068217, International Search Report mailed Oct. 30, 2007", 5 pgs.

"International Application Serial No. PCT/US2007/068217, Written Opinion mailed Oct. 30, 2007", 8 pgs.

Andersen, H, "Long-term follow-up of patients from a randomised trial of atrial versus ventricular pacing for sick-sinus syndrome", *Lancet*, 350(9086), (1997), 1210-1216.

Benchimol, A, "Cardiac hemodynamics during stimulation of the right atrium, right ventricle, and left ventricle in normal and abnormal hearts", *Circulation*, 33(6), (Jun. 1966), 933-44.

Leclercq, C, et al., "Hemodynamic importance of preserving the normal sequence of ventricular activation in permanent cardiac pacing", *Am Heart J.*, 129(6), (1995), 1133-1141.

Loukogeorgakis, S. P., et al., "Remote ischemic preconditioning provides early and late protection against endothelial ischemia-reperfusion injury in humans: role of the autonomic nervous system. ", *J Am Coll Cardiol.*, 46(3), (2005), 450-456.

Meier, B., et al., "Coronary Pacing During Percutaneous Transluminal Coronary Angioplasty", *Therapy and Prevention Cardiac Pacing*, 71(31), (1985), 557-561.

Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.

Rosenqvist, M, "The effect of ventricular activation sequence on cardiac performance during pacing", *Pacing and Electrophysiology*, 19(9), (1996), 1279-1286.

Tsang, A., et al., "Postconditioning: a form of "modified reperfusion" protects the myocardium by activating the phosphatidylinositol 3-kinase-Akt pathway", *Circ Res.*, 95(3), Epub Jul. 8, 2004, 230-232.

Vanagt, Ward Y.R., et al., "Ventricular Pacing for Improving Myocardial Tolerance to Ischemia, Progress Report on Project Guidant-CARIM", (2003), 25 pgs.

Wu, Zhong-Kai, et al., "Ischemic preconditioning suppresses ventricular tachyarrhythmias after myocardial revascularization", *Circulation*, 106(24), (2002), 3091-3096.

Yang, S. M., et al., "Multiple, brief coronary occlusions during early reperfusion protect rabbit hearts by targeting cell signaling pathways,", *Journal of the American College of Cardiology*, 44(5), (2004), 1103-1110.

Zhao, Zhi-Qing, et al., "Inhibition of myocardial injury by ischemic postconditioning during reperfusion: comparison with ischemic preconditioning", *Am J Physiol Heart Circ Physiol*, 285(2), (2003), H579-H588.

"U.S. Appl. No. 11/207,251, Amendment and Response filed Apr. 7, 2009 to Final Office Action mailed Feb. 3, 2009", 11 pgs.

"U.S. Appl. No. 11/207,251, Final Office Action mailed Feb. 3, 2009", 9 pgs.

"U.S. Appl. No. 11/207,251, Non-Final Offce Action mailed Jun. 27, 2008", 8 pgs.

"U.S. Appl. No. 11/207,251, Notice of Allowance mailed May 28, 2009", 4 pgs.

"U.S. Appl. No. 11/207,251, Notice of Allowance mailed Sep. 28, 2009", 4 pgs.

"U.S. Appl. No. 11/207,251, Response filed Sep. 29, 2008 to Non Final Office Action mailed Jun. 27, 2008", 14 pgs.

"International Application Serial No. PCT/US2009/000552, International Search Report mailed Apr. 5, 2009", 4 pgs.

"International Application Serial No. PCT/US2009/000552, Written Opinion mailed Apr. 5, 2009", 9 pgs.

"U.S. Appl. No. 11/030,575, Notice of Allowance mailed Jan. 17, 2007", 7 pgs.

"U.S. Appl. No. 11/030,575, Notice of Allowance mailed Jun. 7, 2007", 7 pgs.

"U.S. Appl. No. 11/129,050, Advisory Action mailed Jul. 14, 2009", 3 pgs.

"U.S. Appl. No. 11/129,050, Advisory Action mailed Jul. 28, 2008", 3 pgs.

"U.S. Appl. No. 11/129,050, Final Office Action mailed Apr. 21, 2009", 10 pgs.

"U.S. Appl. No. 11/129,050, Final Office Action mailed May 12, 2008", 8 pgs.

"U.S. Appl. No. 11/129,050, Non-Final Office Action mailed Nov. 6, 2008", 7 pgs.

"U.S. Appl. No. 11/129,050, Non-Final Office Action mailed Nov. 26, 2007", 7 pgs.

"U.S. Appl. No. 11/129,050, Notice of Allowance mailed Aug. 24, 2009", 7 pgs.

"U.S. Appl. No. 11/129,050, Response filed Feb. 23, 2009 to Non-Final Office Action mailed Nov. 6, 2008", 13 pgs.

"U.S. Appl. No. 11/129,050, Response filed Feb. 26, 2008 to Non-Final Office Action mailed Nov. 26, 2007", 14 pgs.

"U.S. Appl. No. 11/129,050, Response filed Jun. 22, 2009 to Final Office Action mailed Apr. 21, 2009", 9 pgs.

"U.S. Appl. No. 11/129,050, Response filed Jul. 14, 2008 to Final Office Action mailed May 12, 2008", 13 pgs.

"U.S. Appl. No. 11/129,050, Response filed Sep. 28, 2007 to Restriction Requirement mailed Aug. 1, 2007", 11 pgs.

"U.S. Appl. No. 11/129,050, Restriction Requirement mailed Aug. 1, 2007", 6 pgs.

"U.S. Appl. No. 11/129,050, Supplemental Response filed Sep. 12, 2008 to Final Office Action mailed May 12, 2008", 12 pgs.

"U.S. Appl. No. 11/129,058, Advisory Action mailed Oct. 17, 2007", 3 pgs.

"U.S. Appl. No. 11/129,058, Appeal Brief filed Jan. 8, 2008", 23 pgs.

"U.S. Appl. No. 11/129,058, Decision on Appeal mailed Nov. 4, 2009", 15 pgs.

"U.S. Appl. No. 11/129,058, Examiner's Answer mailed Jun. 18, 2008", 14 pgs.

"U.S. Appl. No. 11/129,058, Final Office Action mailed Jul. 9, 2007", 12 pgs.

"U.S. Appl. No. 11/129,058, Non-Final Office Action mailed Jan. 29, 2007", 11 pgs.

"U.S. Appl. No. 11/129,058, Response filed Apr. 30, 2007 to Non-Final Office Action mailed Jan. 29, 2007", 16 pgs.

"U.S. Appl. No. 11/129,058, Response filed Oct. 9, 2007 to Final Office Action mailed Jul. 9, 2007", 14 pgs.

"U.S. Appl. No. 11/151,015, Notice of Allowance mailed Dec. 6, 2007", 6 pgs.

"U.S. Appl. No. 11/458,286, Notice of Allowance mailed May 28, 2008", 7 pgs.

"U.S. Appl. No. 11/458,286, Notice of Allowance mailed Nov. 26, 2007", 7 pgs.

"U.S. Appl. No. 11/458,286, Preliminary Amendment mailed Feb. 26, 2008", 7 pgs.

"U.S. Appl. No. 12/250,868, Non-Final Office Action mailed Feb. 8, 2011", 7 pgs.

"U.S. Appl. No. 12/250,868, Non-Final Office Action mailed Nov. 10, 2011", 7 pgs.

"U.S. Appl. No. 12/250,868, Notice of Allowance mailed Jul. 13, 2011", 8 pgs.

"U.S. Appl. No. 12/322,382, Advisory Action mailed Nov. 8, 2011", 3 pgs.

"U.S. Appl. No. 12/322,382, Response filed Oct. 24, 2011 to Final Office Action mailed Aug. 25, 2011", 15 pgs.

"U.S. Appl. No. 12/401,194, Non-Final Office Action mailed Jul. 21, 2011", 11 pgs.

"U.S. Appl. No. 12/401,194, Notice of Allowance mailed Nov. 1, 2011", 11 pgs.

"U.S. Appl. No. 12/401,194, Response filed Jun. 6, 2011 to Restriction Requirement mailed May 4, 2011", 12 pgs.

"U.S. Appl. No. 12/401,194, Restriction Requirement mailed May 4, 2011", 7 pgs.

"U.S. Appl. No. 12/689,016, Non Final Office Action Mailed Dec. 22, 2011", 11 pgs.

"U.S. Appl. No. 13/113,706, Non Final Office Action Mailed Dec. 21, 2011", 6 pgs.

"Arrow Bipolar Pacing Catheters and Pacing Kits", Arrow International, (2000), 4 pgs.

"Australian Application Serial No. 2009209397, First Examiner Report mailed Sep. 1, 2011", 4 pgs.

"Coronary Dilatation Catheters", online]. [archived Mar. 3, 2006]. Retrieved from the Internet: <URL: http://web.archive.org/web/20060303151627/http://www.guidant.com/products/TemplatePDFs/NoPriceDilataticatheters.pdf>, (2006), 3 pgs.

"European Application Serial No. 06717345.0, Office Action mailed May 15, 2009", 2 pgs.

"European Application Serial No. 06717345.0, Response filed Sep. 11, 2009 to Communication mailed May 15, 2009", 7 pgs.

"European Application Serial No. 06752540.2, Communication Mar. 3, 2008", 2 pgs.

"European Application Serial No. 06752540.2, Response filed Apr. 9, 2008 to Communication Mar. 3, 2008", 6 pgs.

"European Application Serial No. 06762527.9, Communication pursuant to Rules 161 to 182 EPC mailed Mar. 3, 2008", 2 pgs.

"European Application Serial No. 06762527.9, Response filed Apr. 9, 2008 to Communication pursuant to Rules 161 to 182 EPC mailed Mar. 3, 2008", 6 pgs.

"Guidant Product Catalog", [online]. [archived Feb. 4, 2005]. Retrieved from the Internet: <URL: http://web.archive.org/web/20050204225345/http://guidant.com/products/VIproductcatalog.pdf>, (2005), 133 pgs.

"International Application Serial No. PCT/US2006/000125, International Search Report and Written Opinion mailed May 11, 2006", 12 pgs.

"International Application Serial No. PCT/US2006/000125, Written Opinion mailed May 11, 2006", 6 pgs.

"International Application Serial No. PCT/US2006/018497, International Search Report mailed Oct. 24, 2006", 5 pgs.

"International Application Serial No. PCT/US2006/018497, Written Opinion mailed Oct. 24, 2006", 7 pgs.

"International Application Serial No. PCT/US2006/018642, International Search Report and Written Opinion mailed Oct. 24, 2006", 14 pgs.

"International Application Serial No. PCT/US2009/001674, International Search Report mailed Nov. 5, 2009", 5 pgs.

"International Application Serial No. PCT/US2009/001674, Written Opinion mailed Nov. 5, 2009", 8 pgs.

"Japanese Application Serial No. 2007-550428, Response filed Nov. 1, 2011 to Office Action mailed Aug. 3, 2011", (w/ English Translation of Amended Claims), 6 pgs.

"Japanese Application Serial No. 2008-508872, Office Action mailed Oct. 27, 2011", 6 pgs.

"Japanese Application Serial No. 2008-511421, Office Action mailed Nov. 16, 2011", 3 pgs.

"Japanese Application Serial No. 2008-511452, Office Action mailed Nov. 14, 2011", 4 pgs.

"Product Overview: RX ACCULINK Carotid Stent System; RX ACCUNET Embolic Protection System", [online]. [retrieved Apr. 14, 2006]. Retrieved from the Internet: <URL: http://web.archive.org/web/20060414151850/http://www.guidant.com/webapp/emarketing/ppt/acculink/ACCULINK.pdf>, (2005), 23 pgs.

"RX ACCUNET Embolic Protection System", [online]. [retrieved Jan. 11, 2006]. Retrieved from the Internet: <URL: http://www.guidant.com/products/ProductTemplates/ES/accunet.shtml>, (2006), 4 pgs.

"RX ACCUNET Embolic Protection System: Information for Prescribers", [online]. [archived Feb. 5, 2005]. Retrieved from the Internet: <URL: http://web.archive.org/web/20050205044138/http://guidant.com/products/TemplatePDFs/ACCUNET_RX.pdf, (Jan. 6, 2005), 32 pgs.

"VOYAGER RX Coronary Dilatation Catheter", [online]. [retrieved Jan. 11, 2006]. Retrieved from the Internet: <URL: http://www.guidant.com/products/ProductTemplates/VI/RX_US_Voyager_Intro.shtml>, (2006), 2 pgs.

Airaksinen, K. E., et al., "Antiarrhythmic effect of repeated coronary occlusion during balloon angioplasty", J Am Coll Cardiol., 29(5), (Apr. 1997), 1035-1038.

Baynham, Tamara C, et al., "Integrated Catheter and Pulse Generator Systems and Methods", U.S. Appl. No. 11/468,875, filed Aug. 31, 2006, 23 pgs.

Baynham, Tamara C, "Method and Apparatus for Cardiac Protection Pacing", U.S. Appl. No. 11/129,050, filed May 13, 2005, 33 pgs.

Baynham, Tamara C, et al., "Method and Apparatus for Initiating and Delivering Cardiac Protection Pacing", U.S. Appl. No. 11/382,849, filed May 11, 2006, 37 pgs.

Dzwonczyk, R., et al., "Myocardial electrical impedance responds to ischemia and reperfusion in humans", IEEE Transactions on Biomedical Engineering, 51(12), (Dec. 2004), 2206-2209.

Girouard, Steven D., "Pulmonary Vein Stent for Treating Atrial Fibrillation", U.S. Appl. No. 60/298,741, filed Jun. 15, 2001, 14 pgs.

Henriques, Jose P., et al., "Outcome of primary angioplasty for acute myocardial infarction during routine duty hours versus during off-hours", J Am Coll Cardiol, 41(12), (Jun. 18, 2003), 2138-2142.

Ishihara, M., et al., "Implications of prodromal angina pectoris in anterior wall acute myocardial infarction: acute angiographic findings and long-term prognosis", J Am Coll Cardiol., 30(4), (1997), 970-5.

Kin, Hajime, et al., "Postconditioning attenuates myocardial ischemia-reperfusion injury by inhibiting events in the early minutes of reperfusion", Cardiovascular Research, 62(1), (Apr. 1, 2004), 74-85.

Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.

Kis, Adrienn, et al., "Repeated Cardiac Pacing Extends the Time During Which Canine Hearts are Protected Against Ischaemia-induced Arrhythmias: Role of Nitric Oxide", Journal of Molecular and Cellular, vol. 31, No. 6, (1999), 1229-1241.

Kloner, R. A., et al., "Prospective temporal analysis of the onset of preinfarction angina versus outcome: an ancillary study in TIMI-9B", Circulation, 97(11), (1998), 1042-5.

Koning, M M, "Rapid ventricular pacing produces myocardial protection by nonischemic activation of KATP+ channels", Circulation, 93(1), (Jan. 1, 1996), 178-186.

Krayenbuhl, H. P., "Hemodynamics in ischemia. Systolic phase", Z. Kardiol., 73 Suppl 2, [Article in German with English Abstract], (1984), 119-25.

Murry, C. E., et al., "Preconditioning with ischemia: a delay of lethal cell injury in ischemic myocardium", Circulation, 74(5), (1986), 1124-1136.

Ovize, M., et al., "Stretch preconditions canine myocardium.", Am J Physiol., 266(1 Pt 2), (Jan. 1994), H137-46.

Pastore, J. M., "Controlled Delivery of Intermittent Stress Augmentation Pacing for Cardioprotective Effect", U.S. Appl. No. 11/151,015, filed Jun. 13, 2005, 25 pgs.

Pastore, Joseph M, et al., "Method and Apparatus for Delivering Pacing Pulses Using a Coronary Stent", U.S. Appl. No. 11/129,058, filed May 13, 2005, 34 pgs.

Patangay, Ahilash, et al., "Ischemia Detection Using Heart Sound Timing", U.S. Appl. No. 11/625,003, filed Jan. 19, 2007, 69 pgs.

Prinzen, Frits W, "Mapping of regional myocardial strain and work during ventricular pacing: experimental study using magnetic resonance imaging tagging", Journal of the American College of Cardiology, 33(6), (May 1999), 1735-1742.

Solomon, S. D., et al., "Angina pectoris prior to myocardial infarction protects against subsequent left ventricular remodeling", J Am Coll Cardiol., 43(9), (2004), 1511-4.

Vegh, A, et al., "Transient ischaemia induced by rapid cardiac pacing results in myocardial preconditioning", Cardiovascular Research, 25(12), (Dec. 1991), 1051-3.

U.S. Appl. No. 12/689,016, filed Jan. 18, 2010, Method and Apparatus for Delivering Chronic and Post-Ischemia Cardiac Therapies.

U.S. Appl. No. 12/250,868, filed Oct. 14, 2008, Intermittent Stress Augmentation Pacing for Cardioprotective Effect.

U.S. Appl. No. 12/405,990, filed Mar. 17, 2009, Deactivation of Intermittent Pacing Therapy.

"Chinese Application Serial No. 200980103308.6, Office Action mailed Sep. 14, 2012", (w/ English Translation), 18 pgs.

"Japanese Application Serial No. 2010-544360, Response filed Oct. 5, 2012 to Office Action mailed Jun. 5, 2012", (w/ English Translation of Amended Claims), 10 pgs.

"U.S. Appl. No. 12/250,868, Notice of Allowance mailed Mar. 6, 2012", 5 pgs.

"U.S. Appl. No. 12/250,868, Response filed Feb. 10, 2012 to Non-Final Office Action mailed Nov. 10, 2011", 6 pgs.

"U.S. Appl. No. 12/401,194, Response to Rule 312 Communication mailed Feb. 17, 2012", 2 pgs.

"U.S. Appl. No. 12/405,990, Response filed Apr. 25, 2012 to Restriction Requirement mailed Apr. 9, 2012", 10 pgs.

"U.S. Appl. No. 12/405,990, Restriction Requirement mailed Apr. 9, 2012", 6 pgs.

"U.S. Appl. No. 12/689,016, Response to Non-Final Office Action mailed Dec. 22, 2011", 16 pgs.

"Australian Application Serial No. 2009209397, Office Action mailed Mar. 19, 2012", 3 pgs.

"Australian Serial Appl. No. 2009209397, Office Action Response filed Mar. 13, 2012", 14 pgs.

"U.S. Appl. No. 12/405,990, Non Final Office Action mailed Aug. 17, 2012", 11 pgs.

"U.S. Appl. No. 12/689,016, Notice of Allowance mailed Jul. 9, 2012", 5 pgs.

"Australian Application Serial No. 2009209397, Response filed Jun. 1, 2012 to Examiners Report mailed Mar. 19, 2012", 23 pgs.

"Japanese Application Serial No. 2010-544360, Office Action mailed Jun. 5, 2012" (w/ English Translation), 3 pgs.

"U.S. Appl. No. 12/405,990, Notice of Allowance mailed Mar. 14, 2013", 5 pgs.

"U.S. Appl. No. 12/405,990, Response filed Nov. 14, 2012 to Non Final Office Action mailed Aug. 17, 2012", 17 pgs.

* cited by examiner

CONFIGURABLE INTERMITTENT PACING THERAPY

RELATED APPLICATIONS

This application claims the benefit under 35 U.S.C. 119(e) of U.S. Provisional Patent Application Ser. No. 61/024,431, filed on Jan. 29, 2008, which is incorporated herein by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Sometimes patients who receive IMDs have experienced heart failure (HF) decompensation or other events associated with worsening HF. Worsening HF may cause deteriorating hemodynamic performance that could lead to the inability to carry out daily activities and even could lead to death of the patient. Symptoms associated with worsening HF may include progressive decline in ejection fraction called progressive ventricular dilatation. Electrical pacing therapy may prevent progressive ventricular dilatation.

OVERVIEW

This document relates generally to systems, devices, and methods for monitoring hemodynamic parameters of a patient or subject. An apparatus example includes at least one implantable cardiac depolarization sensing circuit, an electrical stimulation circuit, and a pacing mode controller. The implantable cardiac depolarization sensing circuit is configured to obtain a sensed depolarization signal from a ventricle and the electrical stimulation circuit is configured to provide pacing electrical stimulation energy to at least one implantable ventricular electrode. The pacing mode controller is configured to deliver pacing therapy according to a first pacing mode that is a normal operating mode, and to deliver pacing therapy according to second and third pacing modes. The second and third pacing modes increase mechanical stress on at least a particular portion of the ventricle as compared to the pacing therapy delivered during the first pacing mode. The pacing mode controller alternates between the second and third pacing modes when switched from the normal operating mode to a stress augmentation mode.

A method example includes delivering pacing therapy using an implantable device according to a first pacing mode that is a normal operating mode, and delivering pacing therapy according to a second pacing mode and a third pacing mode. The second pacing mode and the third pacing mode increase mechanical stress on at least a particular portion of the ventricle as compared to the pacing therapy delivered during the first pacing mode. The method also includes alternating between the second and third pacing modes when switched from the normal operating mode to a stress augmentation mode.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
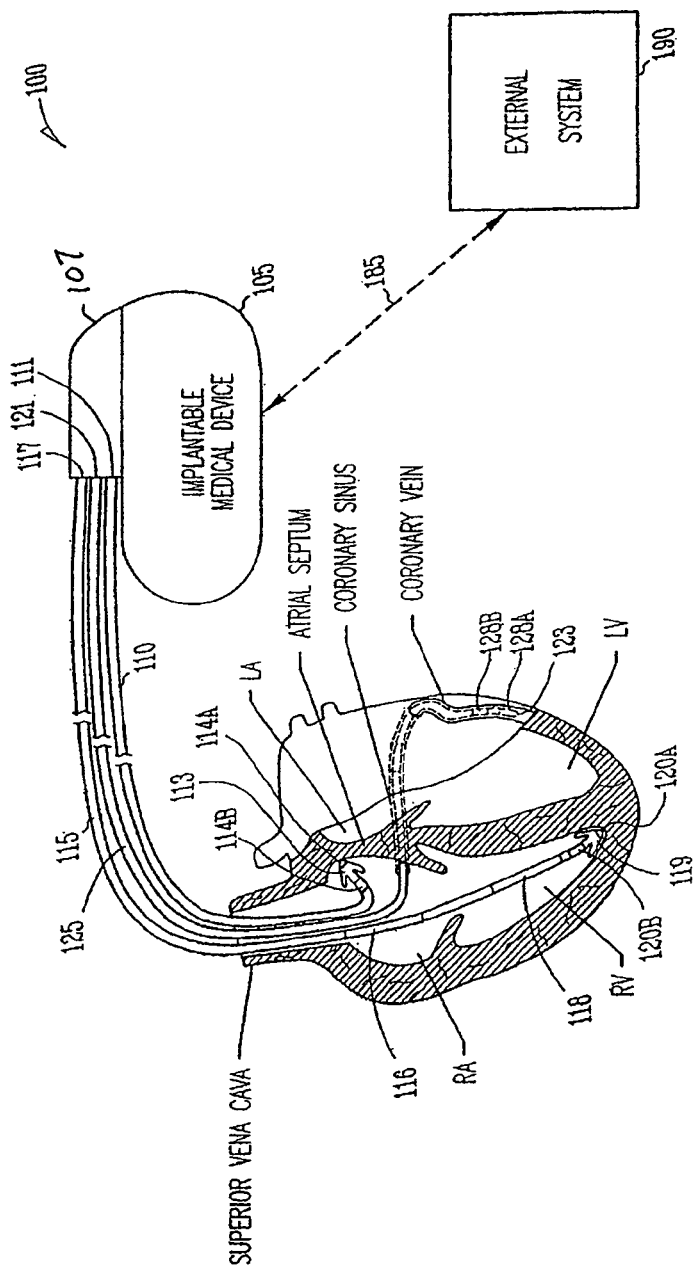
FIG. 1 is an illustration of portions of an example of a system that uses an IMD.

FIG. 1 is an illustration of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

As discussed above, symptoms associated with worsening HF may include progressive ventricular dilatation or a decline in ejection fraction. Occasionally causing dyssynchrony of ventricular contractions may prevent progressive ventricular dilatation. This dyssynchrony may be provided by an intermittent pacing therapy using an IMD. The intermittent pacing therapy is designed to increase ventricular dyssynchrony to cause stress in regional areas of the myocardial wall. The stress is caused in regions that are activated later than others. Providing this intermittent regional stress may halt progression of ventricular dilatation.

Figure 2:
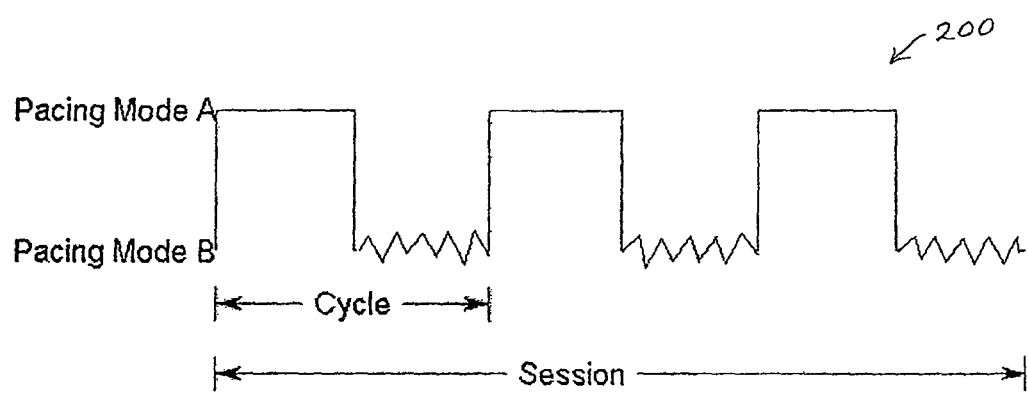
FIG. 2 is an illustration of a timing diagram of an example of intermittent pacing therapy provided by an IMD.

FIG. 2 is an illustration of a timing diagram 200 of an example of intermittent pacing therapy provided by an IMD. The timing diagram 200 shows an intermittent pacing therapy session. Prior to and after the intermittent pacing session, the IMD provides pacing therapy in a normal operating mode that allows for regular depolarizations to occur in the heart chamber (e.g., the North American Society Pacing and Electrophysiology or British Pacing and Electrophysiology Group (NASPE/BPEG)-defined DDD pacing mode). The intermittent pacing session includes three cycles of alternating Pacing Mode A with Pacing Mode B. The alternating of Pacing Mode A with Pacing Mode B increases mechanical stress on at least a particular portion of a ventricle as compared to the pacing therapy delivered during the normal operating mode. This intermittent pacing therapy can be referred to as a stress augmentation mode and is designed to provide control over the progression of ventricular dilatation.

Figure 3:
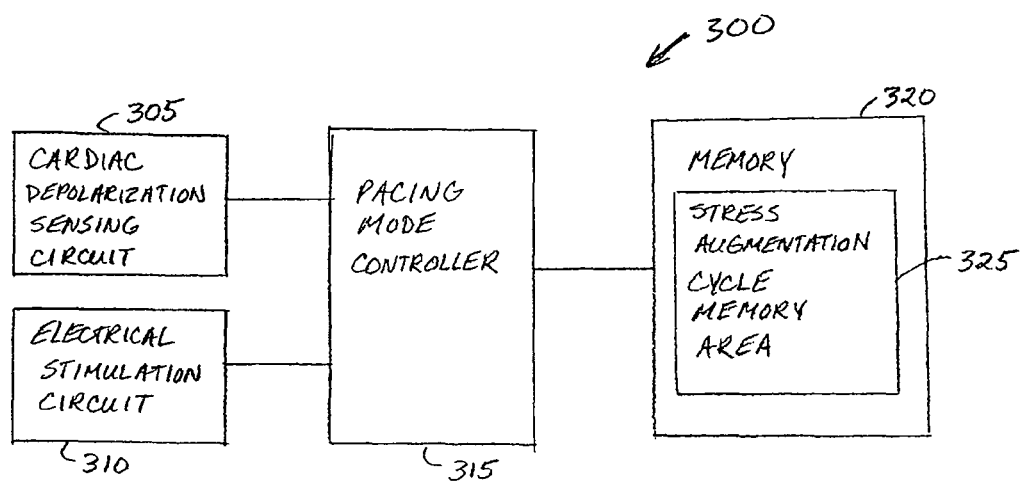
FIG. 3 is a block diagram of portions of an example of an IMD that provides intermittent pacing therapy in a stress augmentation mode.

FIG. 3 is a block diagram of portions of an IMD 300 to provide intermittent pacing therapy in a stress augmentation mode. The IMD 300 includes at least one implantable cardiac depolarization sensing circuit 305, an electrical stimulation circuit 310, and a pacing mode controller 315. The cardiac depolarization sensing circuit 305 obtains a sensed depolarization signal from a ventricle such as by using a sense amplifier circuit for example. The electrical stimulation circuit provides pacing electrical stimulation energy to at least one implantable ventricular electrode.

The pacing mode controller 315 may include a digital signal processor, application specific integrated circuit (ASIC), microprocessor, or other type of processor, interpreting or executing instructions in software or firmware. In some examples, the pacing mode controller 315 may include a state machine or sequencer that is implemented in hardware circuits. The pacing mode controller 315 may include any combination of hardware, firmware, or software. The pacing mode controller 315 includes one or more circuits to perform the functions described herein. A circuit may include software, hardware, firmware or any combination thereof. For example, the circuit may include instructions in software executing on the pacing mode controller 315. Multiple functions may be performed by one or more circuits.

The pacing mode controller 315 is communicatively coupled to the cardiac depolarization sensing circuit 305 and the electrical stimulation circuit 310 (e.g., the pacing mode controller 315 is able to communicate signals with the cardiac depolarization sensing circuit 305 and the electrical stimulation circuit 310 even though there may be intervening circuitry coupled between them.

The pacing mode controller 315 delivers pacing therapy (via the cardiac depolarization sensing circuit 305 and the electrical stimulation circuit 310) according to a first mode that is a normal operating mode. The pacing mode controller 315 also delivers intermittent pacing therapy in a stress augmentation mode.

When switched from the normal operating mode to the stress augmentation mode, the pacing mode controller 315 delivers pacing therapy according to a second pacing mode and a third pacing mode. The second pacing mode and the third pacing mode increase mechanical stress on at least a particular portion of the ventricle as compared to the pacing therapy delivered during the first pacing mode. The pacing mode controller 315 alternates pacing therapy between the second and third pacing modes (e.g., between Pacing mode A and Pacing B in FIG. 2) when switched from the normal operating mode to a stress augmentation mode.

In some examples, the cardiac depolarization sensing circuit 305 is configured to obtain a sensed depolarization signal from an atrium such as by placement of an implantable electrode in or near the atrium, and the electrical stimulation circuit is configured to provide pacing electrical stimulation energy to the atrial electrode. In some examples, the pacing mode controller 315 provides the NASPE/BPEG-defined DDD pacing mode in the normal operating mode.

In some examples, when in the second pacing mode, the pacing mode controller 315 paces at least one ventricle (V), without timing the pacing of the ventricle from an atrial cardiac event, when a V-V interval exceeds a specified ventricular interval (e.g., the NASPE/BPEG-defined VVI pacing mode). In some examples, when in the third pacing mode, the pacing mode controller 315 paces an atrium and, in response to the pace in the atrium, triggers pacing of at least one ventricle after expiration of a specified fixed or dynamic AV delay without regard to any intrinsic cardiac depolarization event occurring in the ventricle (e.g., the NASPE/BPEG-defined DOO pacing mode).

The pacing mode controller 315 includes or is coupled to a memory 320. In some examples, the memory 320 includes a stress augmentation cycle memory area 325 that stores a value that specifies a programmable number of alternating cycles between the second and third pacing modes during the stress augmentation mode before returning to the first pacing mode. In other words, the stored value is the number of times the intermittent pacing alternates between Pacing Mode A and Pacing Mode B during the stress augmentation mode session.

In some examples, the memory 320 includes a second pacing mode cycle length memory area that specifies a duration of the second pacing mode before alternating to the third pacing mode, and a third pacing mode cycle length memory area that specifies the duration of the third pacing mode before alternating to the second pacing mode. The second and third pacing mode memory areas for cycle length are independently programmable to different values. Thus, in FIG. 2, the duration of time spent in Pacing Mode A can be different from the time spent in Pacing Mode B.

In some examples, the stress augmentation cycle memory area 325 specifies the duration of time spent in the stress augmentation mode before automatically switching to the normal operating mode. Thus, in FIG. 2, the length of the stress augmentation mode session is programmable. In some examples, the stress augmentation cycle memory area 325 specifies a duration of time spent in the normal operating mode before automatically switching to the stress augmentation mode. In some examples, the stress augmentation cycle memory area 325 specifies a total number of stress augmentation mode sessions to deliver to the patient. In some examples, the stress augmentation cycle memory area 325 specifies a total number of stress augmentation mode sessions to deliver per day. In some examples, the stress augmentation cycle memory areas specifies a time of day for initiating the stress augmentation mode. In some examples, the stress augmentation cycle memory area specifies a number of days for enabling the stress augmentation mode.

According to some examples, a number of stress augmentation mode sessions as shown in FIG. 2 are delivered in a stress augmentation burst. In some examples, the stress augmentation cycle memory area 325 specifies the number of stress augmentation mode sessions in a stress augmentation burst. In some examples, the stress augmentation cycle memory area 325 specifies the number of stress augmentation bursts per day. In some examples, the stress augmentation cycle memory area 325 specifies the duration of time between stress augmentation mode sessions (e.g., the duration of the normal operating mode between the session in the burst).

Figure 4:
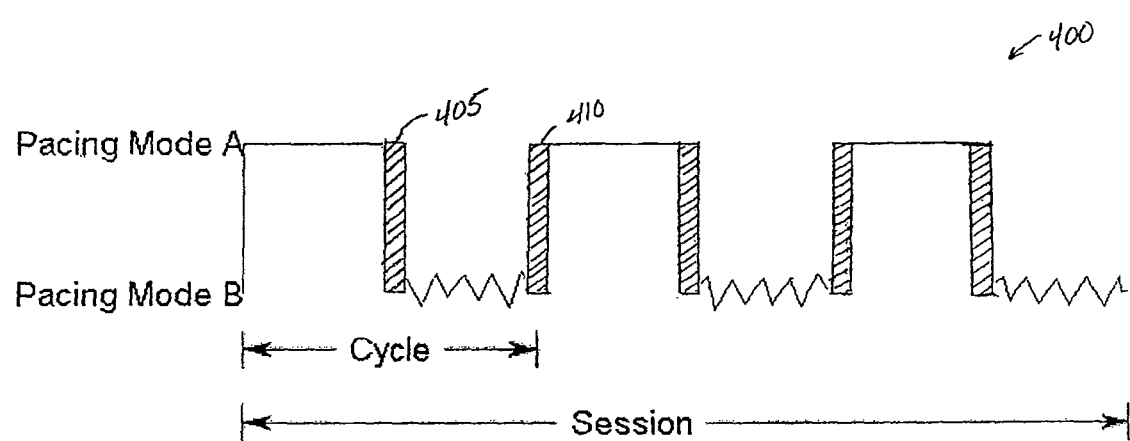
FIG. 4 is an illustration of a timing diagram of another example of intermittent pacing therapy provided by an IMD.

FIG. 4 is an illustration of a timing diagram 400 of another example of intermittent pacing therapy provided by an IMD. In the example, there is a duration of time 405, between the switch from Pacing Mode A to Pacing Mode B, where no pacing energy is delivered by the IMD. There is also duration of time 410 between the switch from Pacing Mode B to Pacing Mode A where no pacing energy is delivered. Thus, in some examples, the stress augmentation cycle memory area 325 specifies the duration of time between the second pacing mode and the third pacing mode during which pacing electrical stimulation energy is not delivered. In some examples, the time durations 405, 410 are separately programmable.

Returning to FIG. 3, the pacing mode controller 315 delivers pacing therapy in the second and third pacing modes using independently programmable pacing parameters. In some examples, the pacing mode controller 315 delivers a different programmable NASPE/BPEG-defined pacing mode in the second pacing mode than the programmable NASPE/BPEG-defined pacing mode in the third pacing mode. In some examples, the pacing mode controller 315 delivers pacing therapy at a different programmable rate in the second pacing mode than in the third pacing mode. In some examples, the IMD 300 includes a plurality of implantable electrodes disposed at sites in or around the heart. The pacing mode controller 315 delivers pacing in the second and/or third pacing modes to one or more different programmable pacing sites.

In some examples, the pacing mode controller 315 delivers pacing at a different programmable pacing amplitude in the second pacing mode than in the third pacing mode. In some examples, the pacing mode controller 315 delivers pacing at a different programmable pacing pulse-width in the second pacing mode than in the third pacing mode.

In some examples, at least one of the second or third pacing modes includes delivering pacing to an atrium and a ventricle. In some examples, the stress augmentation cycle memory area 325 specifies a programmable atrial-ventricular (AV) delay interval for at least one of the second and third pacing modes. In some examples, the electrical stimulation circuit 310 provides pacing electrical stimulation energy to at least one implantable ventricular electrode in the right ventricle (RV) and at least one implantable electrode in the left ventricle (LV). At least one of the second or third pacing modes includes delivering pacing to the pacing mode controller 315 delivers pacing to the RV and LV. In some examples, the stress augmentation cycle memory area 325 specifies a programmable LV offset interval for at least one of the second and third pacing modes.

According to some examples, the stress augmentation mode may be programmed to provide varying degrees of mechanical stress to the regional areas of the myocardial wall. In some examples, the change in stress is provided by the amount the AV delay interval in the stress augmentation mode is shortened from the AV delay interval in the normal mode. In certain examples, a lower level of stress is provided in the stress augmentation mode by shortening the AV delay interval by twenty percent (20%). In certain examples, a medium or nominal level of stress is provided in the stress augmentation mode by shortening the AV delay interval by forty percent (40%). In certain examples, a high level of stress is provided in the stress augmentation mode by shortening the AV delay interval by sixty percent (60%).

In some examples, lower levels of stress may be provided for longer periods of time than higher levels of stress. In certain examples, a stress augmentation mode with a low level of stress may be provided for sixty minutes, and may be provided without cycling the stress augmentation mode on and off. This can be analogized to cardiovascular exercise training, where the intensity of the exercise is lower but the duration of the exercise is long.

In certain examples, a stress augmentation mode with a nominal level of stress may be provided for thirty minutes, and the stress augmentation mode may be cycled on and off. In some examples, cycling off the stress augmentation mode includes providing pacing therapy according to the normal pacing mode during the cycle off time. In some examples, cycling off the stress augmentation mode includes providing no pacing therapy during the cycle off time. In certain examples, a stress augmentation mode with a high level of stress may be provided for fifteen minutes, and the stress augmentation mode may be cycled on and off. This can be analogized to weight training, where the intensity of the exercise is high and the duration of the exercise is short.

In some examples, the stress augmentation cycle memory area 325 of FIG. 3 stores an indication of a level of mechanical stress desired during at least one of the second or third pacing modes. The pacing mode controller 315 specifies an AV delay interval and a time duration of a stress augmentation mode session according to the indication of the desired level of mechanical stress. In certain examples, the AV delay interval and time duration may be included in a lookup table indexed according to desired stress level. In certain examples, the pacing mode controller 315 specifies a cycle on time and a cycle off time during the stress augmentation mode session. Pacing therapy according to the second and/or third pacing mode is provided during the cycle on time, and pacing therapy according to the normal mode or no pacing therapy is provided during the cycle off time.

The automatic specification of intermittent pacing therapy parameters according to the desired stress level may provide ease of programmability of the intermittent pacing therapy for the physician.

In some examples, the stress level for the stress augmentation mode is determined from an indication of a type of heart failure disease pathology. The stress augmentation cycle memory area 325 stores an indication of a heart failure disease pathology of the patient. The pacing mode controller 315 specifies the stress level (e.g., the AV delay interval and the time duration of a stress augmentation mode session) according to the indication of a heart failure disease pathology.

In certain examples, the pacing mode controller 315 specifies a low stress level for a long period of time if the indication is that the patient has HF but has preserved systolic function (PSF). In certain examples, the pacing mode controller 315 specifies a medium or nominal stress level for a medium period of time with on and off cycling if the indication is that the patient has had an ischemic episode. In certain examples, the pacing mode controller 315 specifies a high stress level for a short period of time with on an off cycling if the indication is that the patient has dilated cardiomyopathy (DCM).

It may be desirable to alter the NASPE/BPEG-defined pacing modes of the second and third pacing mode during the stress augmentation mode. In some examples, the pacing mode controller 315 is configured to alter the NASPE/BPEG-defined pacing mode of at least one of the second pacing mode and the third pacing mode during the stress augmentation mode. For example, either the second or third pacing mode may be changed from the NASPE/BPEG-defined VVI pacing mode to the NASPE/BPEG-defined VOO pacing mode. The pacing mode or modes may be changed between stress augmentation sessions or within a stress augmentation mode session.

According to some examples, the stress augmentation mode consists of more than the second and third pacing modes. The pacing mode controller 315 delivers pacing therapy according to at least one additional pacing mode. Like the second and third pacing mode, the additional pacing mode also increases mechanical stress on at least a particular portion of the ventricle as compared to the pacing therapy delivered during normal operating mode. The pacing mode controller 315 alternates between the second pacing mode, third pacing mode, and the additional pacing mode when switched from the normal operating mode to a stress augmentation mode. For example, in FIG. 2, the stress augmentation mode session would alternate among Pacing Mode A, Pacing Mode B, and a Pacing Mode C.

Figure 5:
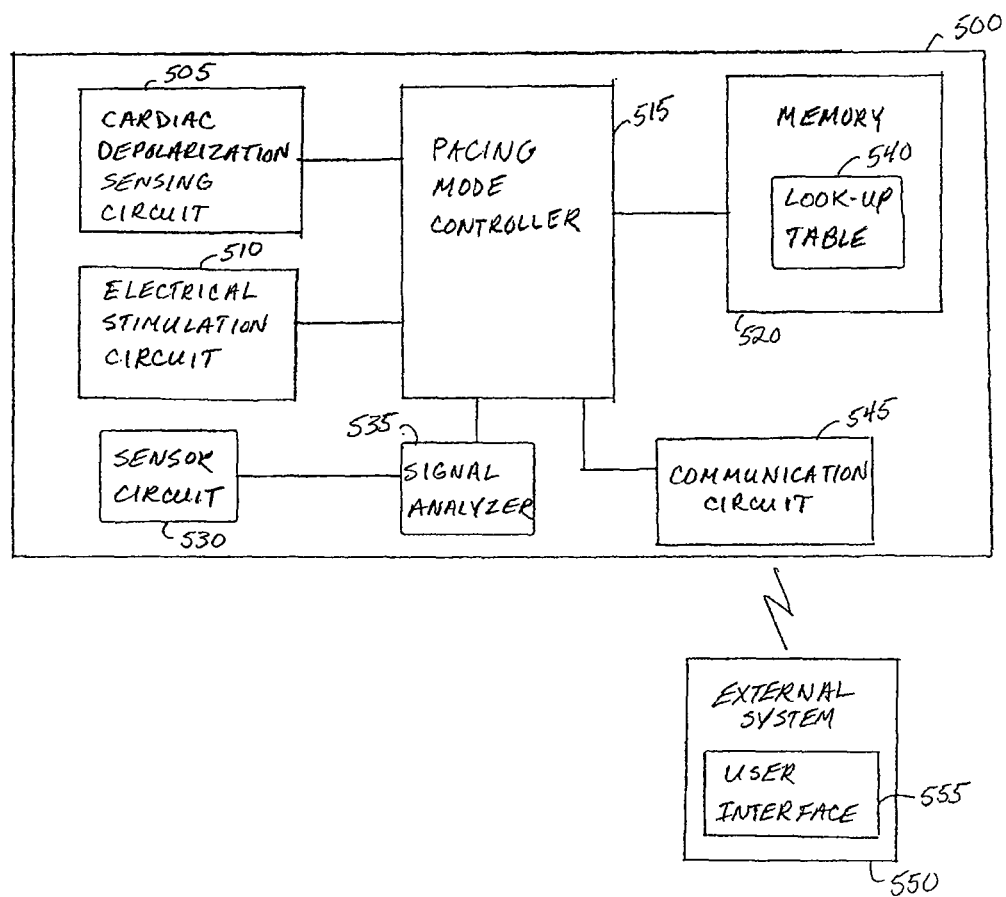
FIG. 5 is a block diagram of portions of another example of an IMD that provides intermittent pacing therapy in a stress augmentation mode.

FIG. 5 is a block diagram of portions of another IMD 500 to provide intermittent pacing therapy in a stress augmentation mode. The IMD 500 includes an implantable cardiac depolarization sensing circuit 505, an electrical stimulation circuit 510, and a pacing mode controller 515. The IMD 500 also includes a sensor circuit 530 and a signal analyzer 535 communicatively coupled to the sensor circuit 530 and the pacing mode controller 515. The sensor circuit 530 produces an electrical sensor signal indicating one or more physiologic cardiovascular events of a subject. The signal analyzer 535 detects, from information provided by the electrical sensor signal, a patient physiologic condition that contraindicates an aspect of the stress augmentation mode. In some examples, the signal analyzer 535 may detect an episode of atrial or ventricular arrhythmia using the signal provided by the electrical sensor signal. The signal analyzer 535 may include an arrhythmia detector that detects a predetermined type or types of arrhythmia. An atrial or ventricular arrhythmia is an example of a patient physiologic condition that contraindicates at least an aspect of the stress augmentation mode. In some examples, the stress augmentation may be contraindicated altogether by the physiologic condition.

In some examples, the pacing mode controller 515 inhibits the stress augmentation mode when the aspect of the stress augmentation mode is contraindicated by the signal analyzer 535. In some examples, the pacing mode controller 515 retries the stress augmentation mode after the stress augmentation mode has been inhibited for a specified time duration. In some examples, the pacing mode controller 515 retries the stress augmentation mode for a specified number of retry attempts before disabling the stress augmentation mode. In some examples, the pacing mode controller 515 automatically alters the stress augmentation mode when the aspect of the stress augmentation mode is contraindicated by the signal analyzer 535. For example, a pacing amplitude may be altered due to the detected physiologic condition.

According to some examples, the IMD 500 includes a memory 520 integral to, or communicatively coupled to, the pacing mode controller 515. The memory 520 stores a lookup table 540 of NASPE/BPEG-defined pacing modes. When the second or third pacing modes is contraindicated by the physiological condition detected using the signal analyzer 535, the pacing mode controller 515 replaces at least one of the second or third pacing modes with a different pacing mode from the lookup table 540. For example, the pacing mode controller 515 may change the third pacing mode from DOO to VOO based on the detected physiologic condition. In some examples, the look up table 540 only includes the NASPE/BPEG-defined pacing modes deemed appropriate for the patient. In other words, those NASPE/BPEG-defined pacing modes that are contraindicated are not included.

FIG. 5 also shows an external system 550 used to communicate with the IMD 500. The IMD 500 includes a communication circuit 545 coupled to the pacing mode controller 515 to communicate wirelessly with the external system 550. The external system 550 includes a user interface 555 to configure one or more parameters of the stress augmentation pacing feature. For example, the user interface 555 may display a table of parameters for a physician to fill in, or may display default parameters for the physician to alter. The external system 550 then transmits the parameters to the IMD 500 for storage in a stress augmentation cycle memory area included in the memory 520.

Figure 6:
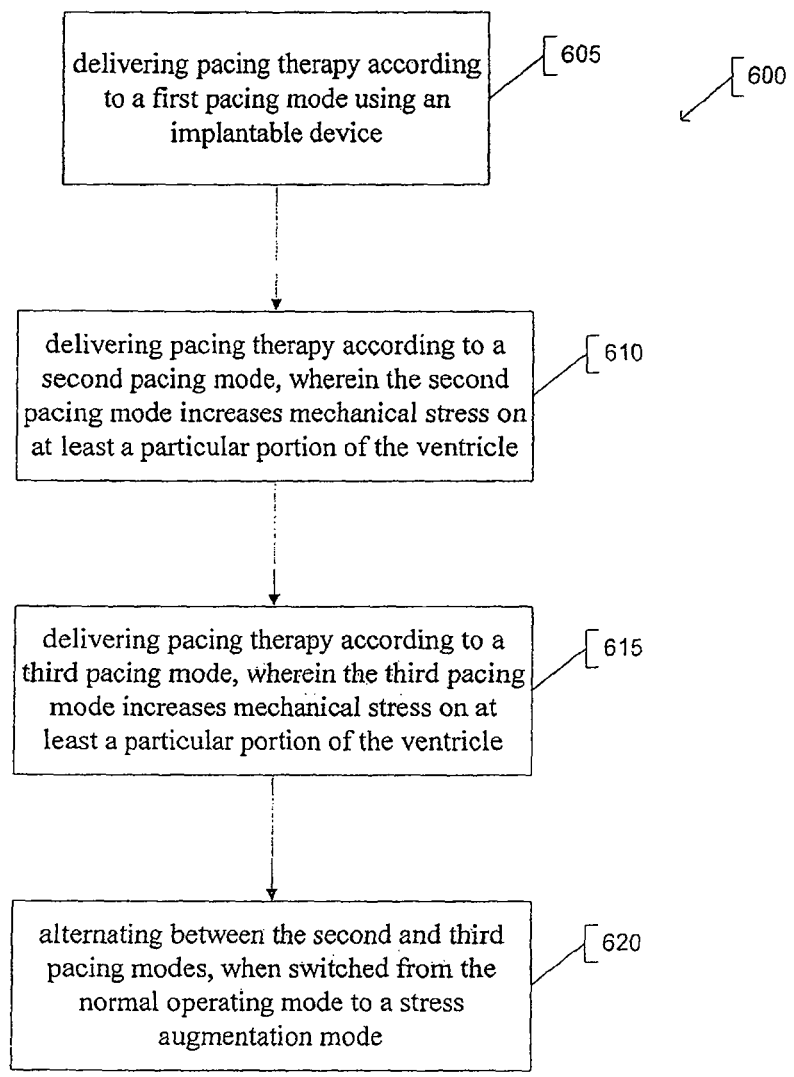
FIG. 6 is a flow diagram of an example of a method of providing intermittent pacing therapy in a stress augmentation mode.

FIG. 6 is a flow diagram of an example of a method 600 of providing intermittent pacing therapy in a stress augmentation mode. At block 605, pacing therapy is delivered according to a first pacing mode using an IMD. The first pacing is a normal operating mode that allows for regular depolarizations to occur in the heart chamber (e.g., the NASPE/BPEG-defined DDD pacing mode).

At block 610, pacing therapy is delivered by the according to a second pacing mode using the IMD. The second pacing mode increases mechanical stress on at least a particular portion of the ventricle as compared to the pacing therapy delivered during the first pacing mode. At block 615, pacing therapy is delivered according to a third pacing mode by the IMD. The third pacing mode also increases mechanical stress on at least a particular portion of the ventricle as compared to the pacing therapy delivered during the first pacing mode.

At block 620, when the IMD is switched from the normal operating mode to a stress augmentation mode, the pacing therapy alternates between the second and third pacing modes. The intermittent pacing that alternates between the second and third pacing modes is designed to increase ventricular dyssynchrony to cause stress in regional areas of the myocardial wall. Providing this intermittent regional stress stops the deterioration of hemodynamic performance of a HF patient, such as by stopping the progression of ventricular dilatation for example.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:
1. An apparatus comprising:
 at least one implantable cardiac depolarization sensing circuit, configured to obtain a sensed depolarization signal from a ventricle;
 an electrical stimulation circuit, configured to provide pacing electrical stimulation energy to at least one implantable ventricular electrode; and a pacing mode controller communicatively coupled to the cardiac depolarization sensing circuit and the electrical stimulation circuit, wherein the pacing mode controller is configured to:
deliver pacing therapy according to a first pacing mode, wherein the first pacing mode is included in a normal operating mode;
deliver pacing therapy according to a second pacing mode, wherein the second pacing mode monitors intrinsic cardiac events differently than in the first pacing mode, triggers or inhibits delivery of pacing pulses according to intrinsic cardiac events differently than in the first pacing mode, and increases mechanical stress on at least a particular portion of the ventricle as compared to the pacing therapy delivered during the first pacing mode;
deliver pacing therapy according to a third pacing mode, wherein the third pacing mode monitors intrinsic cardiac events differently than in both the first pacing mode and the second pacing mode, triggers or inhibits delivery of pacing pulses according to intrinsic cardiac events differently than in both the first pacing mode and the second pacing mode, and increases mechanical stress on at least a particular portion of the ventricle as compared to the pacing therapy delivered during the first pacing mode; and
alternate between the second and third pacing modes when switched from the normal operating mode to a stress augmentation mode.

2. The apparatus of claim 1, wherein the pacing mode controller includes or is coupled to a stress augmentation cycle memory area that is configured to store a value that specifies a programmable number of alternating cycles between the second and third pacing modes during the stress augmentation mode before returning to the first pacing mode to deliver pacing therapy according to the first pacing mode.

3. The apparatus of claim 2, wherein the pacing mode controller includes or is coupled to:
a second pacing mode cycle length memory area that is configured to specify a duration of the second pacing mode before alternating to the third pacing mode;
a third pacing mode cycle length memory area that is configured to specify a duration of the third pacing mode before alternating to the second pacing mode; and
wherein the second and third pacing mode memory areas are independently programmable to different values.

4. The apparatus of claim 1, wherein the pacing mode controller includes or is coupled to:
a stress augmentation cycle memory area that is configured to specify at least one of:
a duration of time spent in the stress augmentation mode before automatically switching to the normal operating mode;
a duration of time spent in the normal operating mode before automatically switching to the stress augmentation mode;
a number of stress augmentation mode sessions;
a number of stress augmentation mode sessions per day;
a number of stress augmentation mode sessions in a stress augmentation burst;
a number of stress augmentation bursts per day;
a duration of time between stress augmentation mode sessions;
a duration of time between the second pacing mode and the third pacing mode during which pacing electrical stimulation energy is not delivered;
a number of days for enabling the stress augmentation mode; and
a time of day for initiating the stress augmentation mode.

5. The apparatus of claim 1, wherein the second pacing mode and the third pacing mode provide stress augmentation through one or more independently programmable pacing parameters that include at least one of: a pacing site; a cardiac sensing site; a pacing trigger condition; a pacing rate; a pacing amplitude; a pacing pulse-width; an atrial-ventricular (AV) delay interval; or left ventricular (LV) offset interval.

6. The apparatus of claim 1, wherein the pacing mode controller is configured to alter the pacing mode of at least one of the second pacing mode and the third pacing mode during the stress augmentation mode.

7. The apparatus of claim 1, wherein the pacing mode controller is configured to:
deliver pacing therapy according to at least one additional pacing mode, wherein the additional pacing mode increases mechanical stress on at least a particular portion of the ventricle as compared to the pacing therapy delivered during the first pacing mode; and
alternate between the second pacing mode, third pacing mode, and the additional pacing mode when switched from the normal operating mode to a stress augmentation mode.

8. The apparatus of claim 1, comprising:
a sensor circuit, configured to produce an electrical sensor signal indicating one or more physiologic cardiovascular events of a subject; and
a signal analyzer, communicatively coupled to the sensor circuit and the pacing mode controller, the signal analyzer configured to detect, from information provided by the electrical sensor signal, a patient physiologic condition that contraindicates an aspect of the stress augmentation mode.

9. The apparatus of claim 8, wherein the pacing mode controller is configured to inhibit the stress augmentation mode when the aspect of the stress augmentation mode is contraindicated by the signal analyzer.

10. The apparatus of claim 9, wherein the pacing mode controller is configured to retry the stress augmentation mode after the stress augmentation mode has been inhibited for a specified time duration.

11. The apparatus of claim 10, wherein the pacing mode controller is configured to retry the stress augmentation mode for a specified number of retry attempts before disabling the stress augmentation mode.

12. The apparatus of claim 9, wherein the pacing mode controller is configured to automatically alter the stress augmentation mode when the aspect of the stress augmentation mode is contraindicated by the signal analyzer.

13. The apparatus of claim 9, including:
a memory, communicatively coupled to the pacing mode controller, to store a lookup table of pacing modes, wherein a pacing mode specifies a cardiac pacing site, a cardiac sensing site, and a pacing trigger condition, and
wherein the pacing mode controller is configured to replace at least one of the second or third pacing modes with a different pacing mode from the lookup table when the second or third pacing modes is contraindicated by the signal analyzer.

14. The apparatus of claim 1, wherein the implantable cardiac depolarization sensing circuit is configured to obtain a sensed depolarization signal from an atrium;
wherein the electrical stimulation circuit is configured to provide pacing electrical stimulation energy to at least one implantable atrial electrode;

wherein the second pacing mode includes pacing at least one ventricle (V), without timing the pacing of the ventricle from an atrial cardiac event, when a V-V interval exceeds a specified ventricular interval; and wherein the third pacing mode includes pacing an atrium and, in response thereto, triggering pacing of at least one ventricle after expiration of a specified fixed or dynamic AV delay without regard to any intrinsic cardiac depolarization event occurring in the ventricle.

15. The apparatus of claim 1, wherein the pacing mode controller includes or is coupled to a stress augmentation cycle memory area that is configured to store an indication of a level of mechanical stress desired during at least one of the second or third pacing mode, and wherein the pacing mode controller is configured to specify an AV delay interval and a time duration of a stress augmentation mode session according to the indication of the desired level of mechanical stress.

16. The apparatus of claim 1, wherein the pacing mode controller includes or is coupled to a stress augmentation cycle memory area that is configured to store an indication of a heart failure disease pathology and wherein the pacing mode controller is configured to specify an AV delay interval and a time duration of a stress augmentation mode session according to the indication of a heart failure disease pathology.

17. A method comprising:
delivering pacing therapy according to a first pacing mode using an implantable device, wherein the first pacing mode is included in a normal operating mode;
delivering pacing therapy according to a second pacing mode, wherein the second pacing mode senses intrinsic cardiac events differently than in the first pacing mode, triggers or inhibits delivery of pacing pulses according to intrinsic cardiac events differently than in the first pacing mode, and increases mechanical stress on at least a particular portion of the ventricle as compared to the pacing therapy delivered during the first pacing mode;
delivering pacing therapy according to a third pacing mode, wherein the third pacing mode monitors intrinsic cardiac events differently than in both the first pacing mode and the second pacing mode, triggers or inhibits delivery of pacing pulses according to intrinsic cardiac events differently than in both the first pacing mode and the second pacing mode, and increases mechanical stress on at least a particular portion of the ventricle as compared to the pacing therapy delivered during the first pacing mode; and
alternating between the second and third pacing modes, when switched from the normal operating mode to a stress augmentation mode.

18. The method of claim 17, wherein alternating between the second and third pacing modes includes alternating between the second and third pacing modes for a specified number of cycles before returning to the first pacing mode to deliver pacing therapy according to the first pacing mode.

19. The method of claim 18, including:
delivering pacing therapy according to the second pacing mode for a first specified duration before alternating to the third pacing mode; and
delivering pacing therapy according to the third pacing mode for a second specified duration before alternating to the second pacing mode, wherein the first and second durations are independently programmable to different values.

20. The method of claim 17, including:
delivering a specified number of stress augmentation mode sessions in a stress augmentation burst; and
delivering a specified number of stress augmentation bursts per day.

21. The method of claim 17, including altering a pacing mode of at least one of the second pacing mode and the third pacing mode during the stress augmentation mode.

22. The method of claim 17, including:
delivering pacing therapy according to at least one additional pacing mode, wherein additional pacing mode increases mechanical stress on at least a particular portion of the ventricle as compared to the pacing therapy delivered during the first pacing mode; and
alternating between the second pacing mode, third pacing mode, and the additional pacing mode when switched from the normal operating mode to a stress augmentation mode.

23. The method of claim 17, wherein delivering pacing therapy according to the second pacing mode and the third pacing mode includes pacing using independently programmable parameters that include at least one of: a pacing site, a cardiac sensing site, a pacing trigger condition, a pacing rate, a pacing amplitude, a pacing pulse-width, an atrial-ventricular (AV) delay interval, or a left ventricular (LV) offset interval.

24. The method of claim 17, including detecting, using the implantable device, a patient physiologic condition that contraindicates an aspect of the stress augmentation mode.

25. The method of claim 24, including inhibiting the stress augmentation mode when the aspect of the stress augmentation mode is contraindicated by the signal analyzer.

26. The method of claim 25, including retrying the stress augmentation mode after the stress augmentation mode has been inhibited for a specified time duration.

27. The method of claim 24, including retrying the stress augmentation mode for a specified number of retry attempts before disabling the stress augmentation mode.

28. The method of claim 24, including altering the stress augmentation mode when the aspect of the stress augmentation mode is contraindicated by the signal analyzer.

29. The method of claim 28, wherein altering the stress augmentation mode includes replacing at least one of the second pacing mode or the third pacing mode with a different pacing mode from a lookup table stored in the implantable device.

30. The method of claim 17,
wherein delivering pacing therapy according to the second pacing mode includes pacing at least one ventricle (V), without timing the pacing of the ventricle from an atrial cardiac event, when a V-V interval exceeds a specified ventricular interval; and
wherein delivering pacing therapy according to the third pacing mode includes pacing an atrium and, in response thereto, triggering pacing of at least one ventricle after expiration of a specified fixed or dynamic AV delay without regard to any intrinsic cardiac depolarization event occurring in the ventricle.

31. The method of claim 17 including,
receiving, into the implantable device, an indication of a desired level of mechanical stress for at least one of the second pacing mode or the third pacing mode; and
determining a decrease in AV delay and a duration of a stress augmentation mode session according to the indication.

32. An apparatus comprising:
an implantable cardiac depolarization sensing circuit, configured to obtain a sensed depolarization signal from a ventricle;

an electrical stimulation circuit, configured to provide pacing electrical stimulation energy to at least one implantable ventricular electrode and to at least one implantable atrial electrode; and a pacing mode controller communicatively coupled to the cardiac depolarization sensing circuit and the electrical stimulation circuit, wherein the pacing mode controller is configured to:

deliver pacing therapy according to a first mode, wherein the first mode is a normal operating mode;

deliver pacing therapy according to a second pacing mode, wherein the second pacing mode increases mechanical stress on at least a particular portion of the ventricle as compared to the pacing therapy delivered during the first pacing mode, wherein the second pacing mode excludes pacing an atrium and includes pacing at least one ventricle (V), without timing the pacing of the at least one ventricle from an atrial cardiac event, when a pace V-V interval exceeds a specified ventricular interval without an intervening sensed intrinsic ventricular event;

deliver pacing therapy according to a third pacing mode, wherein the third pacing mode increases mechanical stress on at least a particular portion of the ventricle as compared to the pacing therapy delivered during the first pacing mode, wherein the third pacing mode includes pacing an atrium and, in response thereto, triggering pacing of at least one ventricle after expiration of the specified fixed or dynamic AV delay without regard to any intrinsic cardiac depolarization event occurring in the ventricle;

alternate between the second and third pacing modes when switched from the normal operating mode to a stress augmentation mode; and wherein the pacing mode controller is configured to deliver a programmable number of stress augmentation mode sessions as a stress augmentation burst and to deliver a programmable number of stress augmentation bursts per day.

33. The apparatus of claim 1, wherein the first pacing mode includes triggering pacing of at least one ventricle after expiration of a specified fixed or dynamic AV delay following a sensed intrinsic or paced atrial cardiac event and inhibiting the pacing of the at least one ventricle when an intrinsic ventricular event is sensed in the at least one ventricle prior to expiration of the specified fixed or dynamic AV delay, wherein the second pacing mode excludes pacing of an atrium and includes triggering pacing of at least one ventricle (V), without timing the pacing of the at least one ventricle from an atrial cardiac event, when a V-V interval exceeds a specified ventricular interval unless an intrinsic ventricular event is sensed prior to expiration of the specified V-V interval, and wherein the third pacing mode includes pacing an atrium without regard to any intrinsic cardiac depolarization event occurring in the atrium and, in response to the pacing, triggering pacing of at least one ventricle after expiration of the specified fixed or dynamic AV delay without regard to any intrinsic cardiac depolarization event occurring in the ventricle.

34. The apparatus of claim 33, wherein the pacing mode controller is configured to change the second pacing mode to a pacing mode that includes triggering pacing of the at least one ventricle (V), without timing the pacing of the at least one ventricle from an atrial cardiac event and without regard to any intrinsic cardiac depolarization event occurring in the ventricle.

35. The apparatus of claim 33, wherein the pacing mode controller is configured to change the third pacing mode to a pacing mode that includes triggering pacing of at least one ventricle (V), without timing the pacing of the at least one ventricle from an atrial cardiac event and without regard to any intrinsic cardiac depolarization event occurring in the ventricle.

* * * * *